US011443850B2

United States Patent
Harpale

(10) Patent No.: US 11,443,850 B2
(45) Date of Patent: Sep. 13, 2022

(54) MAX-MARGIN TEMPORAL TRANSDUCTION FOR AUTOMATIC PROGNOSTICS, DIAGNOSIS AND CHANGE POINT DETECTION

(71) Applicant: General Electric Company, Schenectady, NY (US)

(72) Inventor: Abhay Harpale, San Ramon, CA (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1334 days.

(21) Appl. No.: 15/634,042

(22) Filed: Jun. 27, 2017

(65) Prior Publication Data

US 2018/0373841 A1    Dec. 27, 2018

(51) Int. Cl.
*G06N 20/10* (2019.01)
*G06N 20/00* (2019.01)
(Continued)

(52) U.S. Cl.
CPC ......... *G16H 50/20* (2018.01); *G05B 23/0283* (2013.01); *G06N 7/08* (2013.01);
(Continued)

(58) Field of Classification Search
CPC ........ G16H 50/20; G16H 50/50; G16H 50/00; G06N 20/00; G06N 20/10; G06N 7/08;
(Continued)

(56) References Cited

U.S. PATENT DOCUMENTS 8,306,610 B2 * 11/2012 Mirow .................. G16H 10/20
                                                                600/509
8,988,236 B2    3/2015 Liu
(Continued)

FOREIGN PATENT DOCUMENTS

CN    101685295 A    3/2010
EP      2172887 A2    4/2010

OTHER PUBLICATIONS

Parrado-Hernández, Emilio, Vanessa Gómez-Verdejo, et al. "Discovering brain regions relevant to obsessive-compulsive disorder identification through bagging and transduction." Medical image analysis 18, No. 3 (2014): 435-448 (Year: 2014).*

(Continued)

*Primary Examiner* — Kamran Afshar
*Assistant Examiner* — Randall K. Baldwin
(74) *Attorney, Agent, or Firm* — Wood IP LLC

(57) ABSTRACT

A method of detecting status changes, and a corresponding point-in-time, in monitored entities, includes receiving one or more elements of time-series data from one or more sensors, the elements of time-series data representing an operational state of the monitored entity, creating a predictive model from the time-series data in a datastore memory, applying a transduction classifier to the predictive model, the transduction classifier detecting a change from healthy to unhealthy in the time-series data, and the corresponding point-in-time when the change occurred, and providing an identification of the change in the time-series data and the corresponding point-in-time. In some embodiments the transduction classifier can be a maximum margin classifier having a support vector machine component and a temporal transductive component. A system and a non-transitory computer readable medium are also disclosed.

20 Claims, 9 Drawing Sheets

(51) Int. Cl.
*G06N 7/08* (2006.01)
*G16H 50/20* (2018.01)
*G16H 50/00* (2018.01)
*G05B 23/02* (2006.01)
*G16H 50/50* (2018.01)
*A61B 5/00* (2006.01)
*A61B 5/0205* (2006.01)

(52) U.S. Cl.
CPC ............. *G06N 20/00* (2019.01); *G06N 20/10* (2019.01); *G16H 50/00* (2018.01); *G16H 50/50* (2018.01); *A61B 5/0022* (2013.01); *A61B 5/02055* (2013.01); *A61B 5/7267* (2013.01); *A61B 5/7275* (2013.01)

(58) Field of Classification Search
CPC ............. G05B 23/0283; A61B 5/0022; A61B 5/02055; A61B 5/7267; A61B 5/7275
See application file for complete search history.

(56) References Cited

U.S. PATENT DOCUMENTS

| | | | |
|---|---|---|---|
| 2009/0204232 A1 | 8/2009 | Guru et al. | |
| 2009/0204234 A1 | 8/2009 | Sustaeta et al. | |
| 2012/0025997 A1* | 2/2012 | Liu | E21B 47/009 702/6 |
| 2013/0132001 A1 | 5/2013 | Yacout et al. | |
| 2015/0073751 A1 | 3/2015 | Liao et al. | |
| 2015/0088346 A1 | 3/2015 | Lee | |
| 2015/0272509 A1 | 10/2015 | Kwon | |
| 2015/0346066 A1* | 12/2015 | Dutta | G05B 23/0221 702/183 |
| 2016/0154802 A1* | 6/2016 | Yan | G05B 19/4184 707/725 |
| 2016/0161375 A1* | 6/2016 | Harpale | G05B 23/0283 702/183 |

OTHER PUBLICATIONS

Kumar, S. Mohan, and G. Balakrishnan. "Multi resolution analysis for mass classification in digital mammogram using stochastic neighbor embedding." In 2013 International Conference on Communication and Signal Processing, pp. 101-105. IEEE, 2013 (Year: 2013).*
Nguyen, Minh Hoai. "Segment-based svms for time series analysis." (2012) (Year: 2012).*
Godbole, Shantanu, et al. "Document classification through interactive supervision on both document and term labels." Proceedings of PKDD 2004. (Year: 2004).*
Yang, Yiming, et al. "Utility-based information distillation over temporally sequenced documents." Proceedings of the 30th annual international ACM SIGIR conference on Research and development in information retrieval. 2007:31-38 (Year: 2007).*
Tung, Tran et al., "Machine Fault Diagnosis and Prognosis: The State of The Art", International Journal of Fluid Machinery and Systems, vol. 2, No. 1, Jan.-Mar. 2009, (pp. 61-71, 11 total pages).
Pandian, Annamalai et al., "A Review of Recent Trends in Machine Diagnosis and Prognosis Algorithms", International Journal of Computer Information Systems and Industrial Management Applications (IJCISIM), vol. 2, ISSN: 2150-7988, 2010, (pp. 320-328, 9 total pages).
Srivastava, Ashok N. et al., "Software Health Management: a Necessity for safety Critical Systems", Innovations in Systems and Software Engineering, vol. 9, Issue 4, Dec. 2013, DOI: 10.1007/s11334-0212-0, (pp. 219-233, 15 total pages).
Gama, Joao et al., "A Survey on Concept Drift Adaptation", ACM Computing Surveys, vol. 46, No. 4, Article 44, Mar. 2014, ISSSN: 0360-0300, DOI: 10.1145/2523813, URL: http://doi.acm.org/10.1145/2523813, 37pgs.
Rodriguez, Juan J. et al., "Boosting interval based literals", Intelligent Data Analysis, vol. 5, Aug. 2001, IOS Press, ISSN: 1088-467X. URL: http://dl.acm.org/citation.cfm?id=1294134.1294138, (pp. 245-262, 18 total pages).
Xing, Zhengzheng et al., "Early classification in time series", Knowledge and Information Systems, vol. 31, No. 1, 2012, ISSN: 0219-1377, DOI: 10.1007/s10115-011-0400-x. URL: http://dx.doi.org/10.1007/s10115-011-0400-x, (pp. 105-127, 23 total pages).
Radke, Richard J. et al., "Image Change Detection Algorithms: A Systematic Survey", IEEE Transactions on Image Processing, vol. 14, No. 3, Mar. 2005, ISSN: 1057-7149, DOI: 10.1109/TIP.2004.838698. URL: http://dx.doi.org/10.1109/TIP.2004.838698, (pp. 294-307, 14 total pages).
Collobert, Ronan et al., "Large Scale Transductive SVMs", Journal of Machine Learning Research, vol. 7, Dec. 2006, ISSN: 1532-4435. URL: http://dl.acm.org/citation.cfm?id=1248547.1248609, (pp. 1687-1712, 26 total pages).
Zhang, Yang et al., "One-class Classification of Text Streams with Concept Drift", in Data Mining Workshops, IEEE International Conference on Data Mining Workshops, 2008, ICDMW '08, DOI: 10.1109/ICDMW.2008.54, (pp. 116-125, 10 total pages).
Krempl, Georg et al., "Open Challenges for Data Stream Mining Research", SIGKDD Explorations Newsl., vol. 16, Issue 1, Sep. 2014, ISSN: 1931-0145, DOI: 10.1145/2674026.2674028. URL: http://doi.acm.org/10.1145/2674026.2674028, (pp. 1-10, 10 total pages).
Shalev-Shwartz, Shai et al., "Pegasos: primal estimated subgradient solver for SVM", Mathematical Programming, Ser. B, 2011, DOI: 10.1007/s10107-010-0420-4, URL: http://dblp.uni-trier.de/db/journals/mp/mp127.html#Shalev-ShwartzSSC11, (pp. 3-30, 28 total pages).
Chapelle, Olivier et al., "Semi-Supervised Classification by Low Density Separation", Proceedings of the Tenth International Workshop on Artificial Intelligence and Statistics, 2005, (pp. 57-64, 8 total pages).
Chapelle, Olivier "Training a Support Vector Machine in the Primal", Neural Computation, vol. 19, No. 5, 2007, URL: http://dblp.uni-trier.de/db/journals/neco/neco19.html#Chapelle07, (pp. 1155-1178, 24 total pages).
Ning Wang et al., "A Machine Learning Framework for Space Medicine Predictive Diagnostics with Physiological Signals", Aerospace Conference, 2013 IEEE, Mar. 2, 2013, pp. 1-12.
Extended European Search Report from EP Appl. No. 21195244.5, dated Feb. 21, 2022.

* cited by examiner

MAX-MARGIN TEMPORAL TRANSDUCTION FOR AUTOMATIC PROGNOSTICS, DIAGNOSIS AND CHANGE POINT DETECTION

BACKGROUND

It can be desirable to make assessment and/or predictions regarding the operation of a real world physical system, such as an electro-mechanical system—e.g., an aircraft turbine engine. Similarly, in the medical field it can be desirable to make informed predictions regarding the status of a medical patient based on the patient's medical history and current health condition(s).

Early detection of imminent disorders from routine measurements and checkups is an important challenge in the medical and prognostics research community. Multivariate observations from routine doctor visits are typically available for human patients. Similarly, sensor data is typically available through the life of industrial equipment, from an operational to non-operational state. A predictive model can be used to predict a condition of the system or patient. Sensor and monitoring technologies provide accurate data, however, accurately making such assessments and/or predictions based on this accumulated data can be a difficult task.

While change detection and health status detection algorithms have been studied in the past, conventional approaches do not leverage measurements from assets or patients with unknown health statuses to build better models. Missing from the art is an approach that can benefit from measurements with unknown health status. Conventional approaches do not apply transduction (i.e., the act of learning from unlabeled test data—data to be predicted upon), and chronological constraints to ensure that predictions from a model respect the reasonable expectation that a health status of a monitored entity changes from healthy to unhealthy and not the reverse condition.

DETAILED DESCRIPTION

Embodying systems and methods apply temporal transductive learning to time-series data to detect changes, and a corresponding point in time, in monitored physical assets (e.g., a turbine engine, machinery, appliances, industrial equipment, computer systems, etc.) or patients. The techniques are scalable, even in the presence of temporal constraints and non-linear kernels.

The term "monitored entity" refers to either a monitored physical asset, or a monitored patient. It should be readily understood that the invention is not so limited, and that entities of other natures and/or types that can be monitored are within the scope of this disclosure. For example, a monitored entity can be an industrial plant, machinery, computing system, or software system.

The terms "operational, healthy, and functional" can be used interchangeably regardless of the nature and/or type of monitored entity. Similarly, the terms "nonoperational, unhealthy, and nonfunctional" can be used interchangeably regardless of the nature and/or type of monitored entity. It should be readily understood that these terms are not binary states of the monitored entity (e.g., an engine can have reduced efficiency (nonoperational) but still provide full power; a patient can have diabetes (unhealthy), but still participate fully in daily activities).

In accordance with embodiments, if a monitored entity is diagnosed with a failure (non-operational, disorder, etc.), historical data can be examined to detect an early indicator of the failure's cause. Detection of change-points in the historical data can lead to the identification of external stimuli and/or operating conditions that were the root cause for the eventual failure. For example, the doctor may question the exposure of the individual to certain geographies and an engineer might investigate the operating conditions around the time of change.

In some implementations, once the casual external stimuli and/or operating condition is identified, the knowledge can be applied in forecasting whether other monitored entities can experience possible faults.

Historical data on functioning entities can be seldom available. For example, a doctor might get visits from patients that are already symptomatic or ill. Other patients might ignore early onset symptoms until their next routine visit. Similarly, physical assets might experience continued usage till the problem escalates. Once failure occurs, a user might then first complain about non-functioning units. Routine measurements are inexpensive, but expensive investigative analyses are usually not performed on asymptomatic entities. Thus, for most purposes, any asymptomatic entities are assumed to have an unknown health status.

Figure 1:
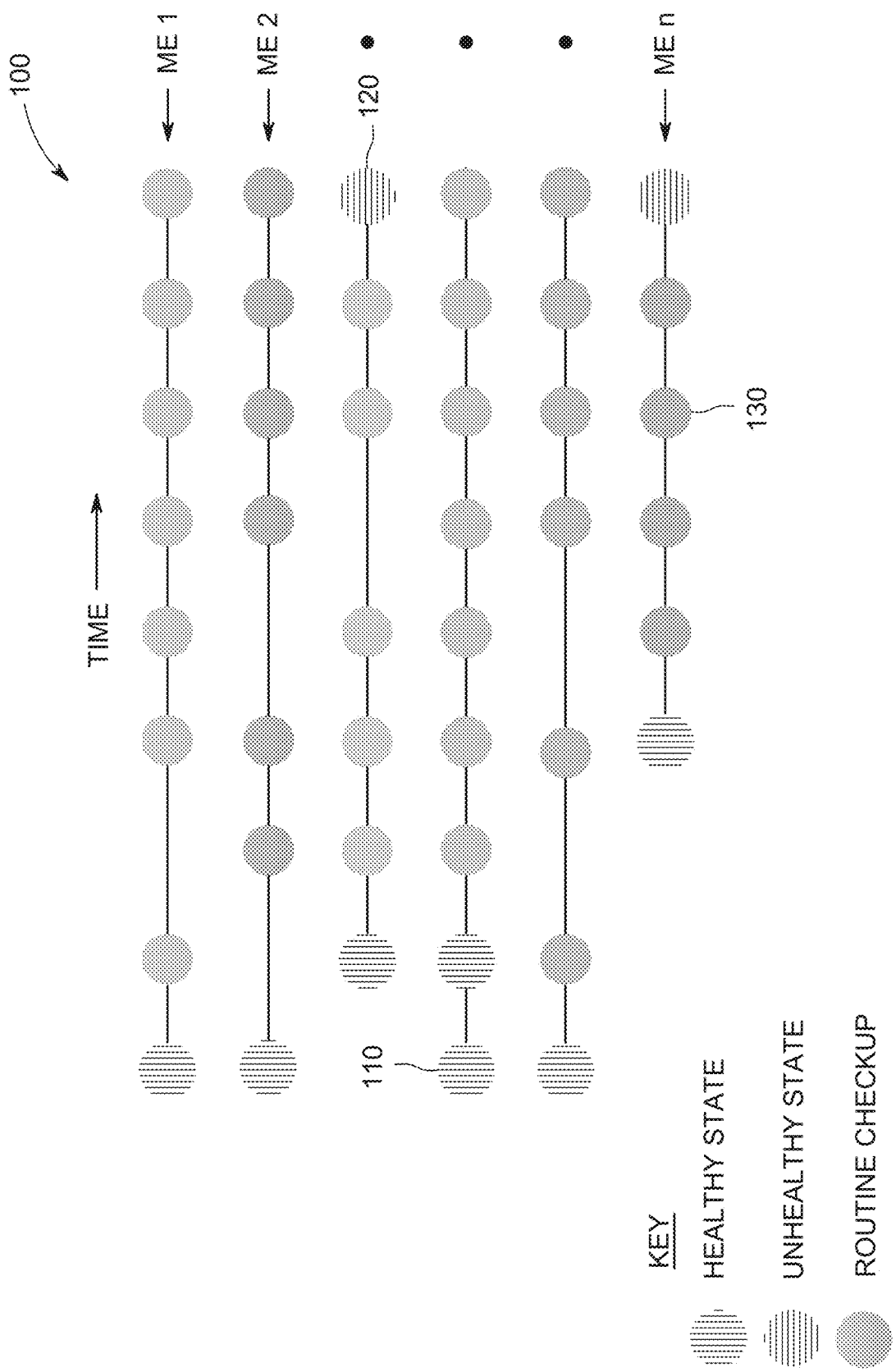
FIG. 1 depicts a representation of a temporal transduction scenario in accordance with embodiments.

FIG. 1 depicts a representation of temporal transduction scenario 100 in accordance with embodiments. Each horizontal row corresponds to the temporal state of a monitored entity ME1, ME2, . . . , MEn. Each circle represents a time of a multivariate measurement, or observation, for that particular monitored entity. Time progresses along the rows from left to right, so that the measurements/observations are chronologically ordered. Measurements 110 indicate that the monitored entity is in a healthy state. Measurements 120 indicate that the monitored entity is in an unhealthy state. Measurements 130 indicate that the status of the monitored entity was made as part of a routine checkup, and that an occurrence of disorder was unknown at that time. The interval between measurements need not be uniform, nor does the quantity of measurements need be equal for each monitored entity.

In accordance with embodiments, monitored entities are initially considered healthy. For a mechanical asset this might be a safe assumption, since every new equipment is thoroughly inspected before being deployed. While doctors might perform a comprehensive examination before admitting a new patient, this assumption might not hold for disorders that exist prior to the initial measurement. Only few monitored entities may have known final unhealthy diagnoses, but the exact occurrence of when the status changed could be unknown.

In accordance with embodiments, transductive learning is applied to model the problem setting with temporal information. Transductive learning is similar to semi-supervised learning, in its use of unlabeled data for inferring a better model with minimal supervision. However, transductive learning differs from semi-supervised learning by using test data as the unlabeled data, instead of any randomly chosen unlabeled data for model inference.

In accordance with embodiments, the model is optimized for better performance on the unlabeled data that is to be predicted upon, not just historical failures used for training. The labeled set can include two parts: the initial measurements from all entities (such as measurement 110) and the final measurements from the entities with known unhealthy states (such as measurement 120). The unlabeled set can include intermediate measurements and final observations from entities with unknown health status (such as measurement 130). In accordance with embodiments, the unlabeled set is classified to (1) classify the final states of monitored entities with unknown final diagnoses to identify those with disorders; and to (2) classify the intermediate observations to identify transitions points (i.e., the time when the entity changed state from healthy to unhealthy). Thus, the unlabeled set is also the test set, hence the transductive learning setting.

In accordance with embodiments, a maximum margin classifier incorporates an support vector machine (SVM) classifier with its transductive counterpart. This embodying classifier is referred to as a Max-Margin Temporal Transduction (MMTT). In addition to traditional constraints for maximum margin classifiers, an embodying MMTT further incorporates a constraint that penalizes violation in the chronology of events—the entity cannot go from unhealthy to healthy without intervention. For scalability, a stochastic gradient descent approach is implemented.

An MMTT classifier can utilize both linear and non-linear kernels. Independent of the kernel, the number of iterations needed to infer an $\epsilon$-accurate model are of the order of $O(1/\lambda\epsilon)$. Experiments on multiple publicly available benchmark datasets, demonstrate that an embodying MMTT classifier provides superior predictive performance with minimal supervision compared to conventional and transductive SVMs.

For purposes of explanation, consider the set of entities $\mathbb{X} = \{x_1, \ldots, x_N\}$. Each entity denotes the element being monitored—a monitored entity. $x_i \in \mathbb{R}^{Ti \times D}$, where D is the dimensionality of the multivariate time-series and $T_i$ is the length of time-series of that particular entity i. Thus, in FIG. 1, i-th row depicts $x_i$ and t-th circle in the i-th row depicts the observation $x_{it}$. Let $\mathbb{Y} = \{y_1, \ldots, y_N\}$ be the health-status or labels for each of the entities, where $y_i \in \{-1, 0, +1\}^{Ti}$. Without loss of generality, -1 denotes healthy (initial) state, +1 denotes unhealthy (changed) state and 0 indicates unknown diagnoses.

The set of entities with known final diagnoses can be denoted by $\mathbb{K} \square \mathbb{X}$, and usually $|\mathbb{K}| << |\mathbb{X}|$. In accordance with embodiments, only entities with a changed final state comprise $\mathbb{K}$, thereby $y_{iTi} = +1, \forall x_i \in \mathbb{K}$. All entities start from the healthy state, thus, $y_{i1} = -1, 1; \forall x_i \in \mathbb{X}$. The training set consists of $\mathbb{X}$, $y_{i1} = -1, 1, \forall x_i \in \mathbb{X}$, and $y_{iTi} = +1, \forall x_i \in \mathbb{K}$.

Embodying systems and methods can provide a final label prediction to identify the health statuses of entities not in $\mathbb{K}$. Specifically, the identification solves $\widehat{y_{iT}} \iota, \forall x_i \in \mathbb{K}^C$, where $\mathbb{K}^C = \mathbb{X} \setminus \mathbb{K}$. The prediction can be denoted by $\widehat{y_{iT}} \iota, \forall x_i \in \mathbb{K}^C$, with the goal of minimizing the prediction error $l(y_{iTi}, \widehat{y_{iT}} \iota)$. In addition to providing a final label prediction, embodying systems and methods also can provide a change-point detection to identify the earliest point of change from healthy to unhealthy state in an unhealthy entity.

In accordance with embodiments, both of these predictions can be addressed by classifying all observations along each entity, $x_{it}, \forall x_{it} \in x_i, x_i \in \mathbb{X}$—i.e., the prediction can be represented as $\widehat{y_{iT}}, \forall i_t$, which results in an entire series prediction. Analyzing the predictions of the entire series can enable the discovery of change-points in the health state of a monitored entity.

Figure 2:
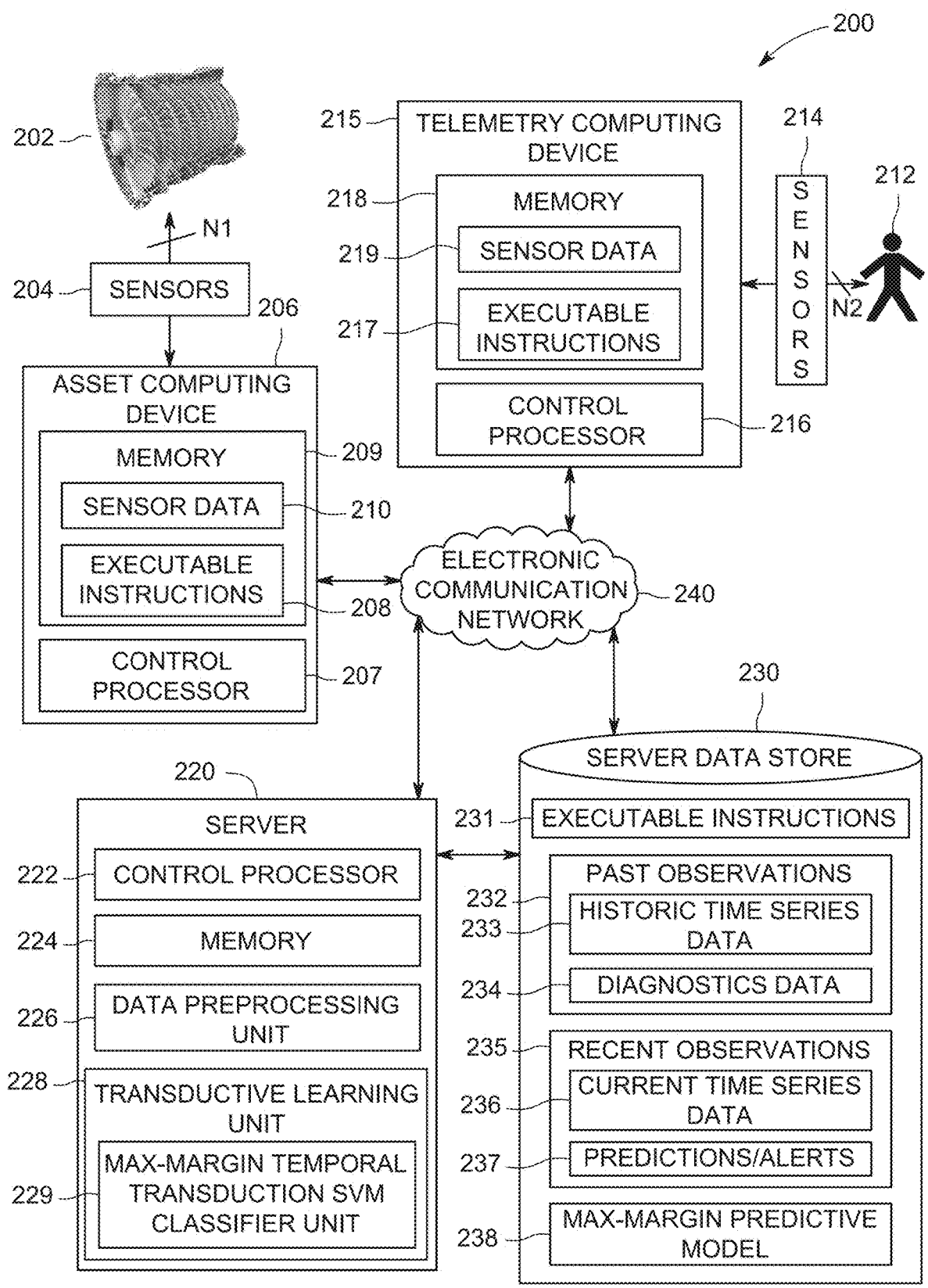
FIG. 2 depicts a system for predicting performance of a monitored entity using a max-margin temporal transduction classifier in accordance with embodiments.

FIG. 2 depicts system 200 for predicting performance of a monitored entity using a MMTT classifier in accordance with embodiments. The MMTT classifier can detect operational status changes and a corresponding point in time in the monitored entity. System 200 can include monitored physical asset 202. Sensors 204 (quantity=N1) can monitor the operational status of monitored physical asset 202. The frequency of data sampling by the sensors can be varied based on factors that include the nature and type of physical asset that is undergoing monitoring. For example for a turbine engine, sensors can monitor turbine vane wear, fuel mixture, power output, temperature(s), pressure(s), etc. Sensor(s) 204 provide data to asset computing device 206. Asset computing device 206 can include control processor 207 that executes executable instructions 208 to control other modules of the asset computing device. Memory 209 can include executable instructions 208 and sensor data records 210.

System 200 can include monitored patient 212. Sensors 214 (quantity=N2) can monitor the physiological state of monitored patient 212. The frequency of data sampling by the sensors can varied based on the particular parameter (e.g., respiratory rate, pulse rate, blood pressure, temperature, etc.). Sensor(s) 214 provide data to telemetry computing device 215. Asset computing device 215 can include control processor 216 that executes executable instructions 217 to control other modules of the telemetry computing device. Memory 218 can include executable instructions 217 and sensor data records 219. For purposes of this discussion one monitored physical entity and one monitored patient is illustrated in FIG. 2, however it is readily understood that system 200 can include multiple monitored entities of any type and nature. Further, embodying systems and methods be implemented regardless of the number of sensors, quantity of data, and format of information received from monitored entities.

In accordance with embodiments, server 220 can obtain multivariate, temporal sensor data from an asset computing device and/or a telemetry computing device across electronic communication network 240. The electronic communication network can be, can comprise, or can be part of, a private internet protocol (IP) network, the Internet, an integrated services digital network (ISDN), frame relay connections, a modem connected to a phone line, a public switched telephone network (PSTN), a public or private data network, a local area network (LAN), a metropolitan area network (MAN), a wide area network (WAN), a wireline or wireless network, a local, regional, or global communication network, an enterprise intranet, any combination of the preceding, and/or any other suitable communication means. It should be recognized that techniques and systems disclosed herein are not limited by the nature of network 240.

Server 220 can include at least one server control processor 222 configured to support embodying MMTT techniques by executing executable instructions 231 accessible by the server control processor from server data store 230. The server can include memory 224 for, among reasons, local cache purposes.

Server 220 can include data preprocessing unit 226 which can apply a stochastic gradient descent based solution to enable scalability. Transductive learning unit 228 can include max-margin temporal transduction SVM classifier unit 229 that can detect operational status changes and a corresponding point in time in the monitored entity sensor data to predict performance.

Data store 230 can include past observation data 232 that contains records of prior accumulated historic time series data 233 and diagnostics data 234. This cumulative data can be organized by unique identifiers associated with individual monitored assets. Recent observations 235 can include current time series data 236 and predictions/alerts 237. Max-margin model 238 is a predictive model of when a monitored entity could change from healthy to unhealthy state.

In accordance with embodiments, a support vector machine (SVM) is extended with a max-margin model represented by Equation 1:

$$\widehat{y_{i_T}}_{i=w} \bullet \phi(X_{it}) \qquad \text{EQ. 1}$$

Where:
$w \in \mathbb{R}^D$ are parameters of the model; and
$\phi(\bullet)$ is a feature transformation.

For inferring $\omega$, the minimization problem of Equation 2 is solved:

$$\underset{f}{\text{minimize}} f(w) := \frac{\lambda}{2} \|w\|^2 + \frac{\ell_L(w)}{|\mathbb{L}|} + \frac{\ell_U(w)}{|\mathbb{U}|} + \frac{\ell_C(w)}{|\mathbb{C}|} \qquad \text{EQ. 2}$$

Where:

$$\ell_L(w) = \sum_{(x,y) \in \mathbb{L}} \max\{0, 1 - y\langle w, \phi(x)\rangle\}$$

$$\ell_U(w) = \sum_{(x,y) \in \mathbb{U}} \max\{0, 1 - |\langle w, \phi(x)\rangle|\}$$

$$\ell_C(w) = \sum_{(x_{i_t}, x_{i_{t+1}}) \in \mathbb{C}} \max\{0, \langle w, \phi(x_{i_t})\rangle - \langle w, \phi(x_{i_{t+1}})\rangle\}$$

$\mathbb{L} = \{(x_{i_t}, y_{i_t}) : x_{i_t} \in \mathbb{X}, y_{i_t} \in \mathbb{Y}, y_{i_t} \neq 0, \forall\}$ $\mathbb{U} = \{(x_{i_t}, y_{i_t}) : x_{i_t} \in \mathbb{X}, y_{i_t} \in \mathbb{Y}, y_{i_t} = 0, \forall\}$ $\mathbb{A} = \mathbb{L} \cup \mathbb{U}$ $\mathbb{C} = \{(x_{i_t}, x_{i_{t+1}}) : x_{i_t} \in \mathbb{A}, x_{i_{t+1}} \in \mathbb{A}\}$ The terms $\ell_L$, $\ell_U$ and $\ell_C$ refer, respectively, to the constraints arising from the labeled, unlabeled and chronological considerations. The hinge-loss ($\ell_L$) is utilized in the context of supervised SVM classifiers. The unlabeled loss ($\ell_U$) can maximize the margin with the help of unlabeled data, a formulation very commonly used in transductive SVMs. The chronological loss ($\ell_C$) can penalize if the chronological constraints are violated. The transition from one state (e.g., operational-to-nonoperational; healthy-to-unhealthy) is strictly a one-way transition. Any violation of the chronological constraint can result in a penalty that needs to be minimized.

In accordance with implementations, chronological loss can be achieved by defining the set $\mathbb{C} = \{(x_{i_t}; x_{i_k}): x_{i_t} \in \mathbb{A}; x_{i_k} \in \mathbb{A}; \forall t < k\}$. Instead of requiring just the local chronological ordering of labels, in some implementations there could be a requirement that the prediction at a particular observation is consistent with all the observations that follow it. While attractive for the linear kernel, this comprehensive loss is likely to be computationally expensive. By design, a localized constraint leads to an efficient streaming algorithm that requires just an observation and its immediate neighbor (i.e., one element of time-series data and the next subsequent element), not the entire series, making it attractive for scalability.

To enable scalability, we propose a stochastic gradient descent based solution for the optimization problem. The sub-gradient at steps of Equation 2, with respect to $w_s$, in the context of a single training example $(x_{i_t}, y_{i_t})$, is expressed as Equation 3:

$$\nabla_s = \lambda w_s + \nabla_s(w_s; x_{i_t}, y_{i_t}) \qquad \text{EQ. 3}$$

Where, $\nabla_s(w_s, x_{i_t}, y_{i_t}) = \mathbb{1}[\langle w_s, \phi(x_{i_t})\rangle > \langle w_s, \phi(x_{i_{t+1}})\rangle]$ $$(\phi(x_{i_t}) - \phi(x_{i_{t+1}})) - \\ \begin{cases} \mathbb{1}[y_{i_t}\langle w_s, \phi(x_{i_t})\rangle < 1] y_{i_t} \phi(x_{i_t}), \text{ if } y_{i_t} \neq 0 \\ \mathbb{1}[|\langle w_s, \phi(x_{i_t})\rangle| < 1] \, sign(\langle w_s, \phi(x_{i_t})\rangle) \phi(x_{i_t}), \text{ otherwise} \end{cases}$$

where $\mathbb{1}[\bullet]$ is the indicator function which takes value 1 only if $\bullet$ is true, else it is 0.

Equipped with this sub-gradient, w can be iteratively learned using the update $w_s+1 \leftarrow w_s - \eta_s \nabla_s$. The term $\eta_s = 1/\lambda s$ can be used, similar to primal estimated sub-gradient solver (PEGASOS) for SVMs. This leads to a stochastic gradient descent (SGD) algorithm, presented in Algorithm 1:

---

ALGORITHM 1

Procedure TTSGD($\mathbb{X}, \lambda, S$)
  $w_0 \leftarrow 0$
  for $s \leftarrow 1, 2, \ldots, S$ do           ▷SGD Iterations
    Choose $i_t \in \{1, \ldots, |\mathbb{A}|\}$ uniformly at random $\eta_s \leftarrow \dfrac{1}{\lambda_s}$ $\delta \leftarrow \lambda w_s$
    if $\langle w_s, \phi(x_{i_t})\rangle > \langle w_s, \phi(x_{i_{t+1}})\rangle$ then

ALGORITHM 1

Figure 3A:
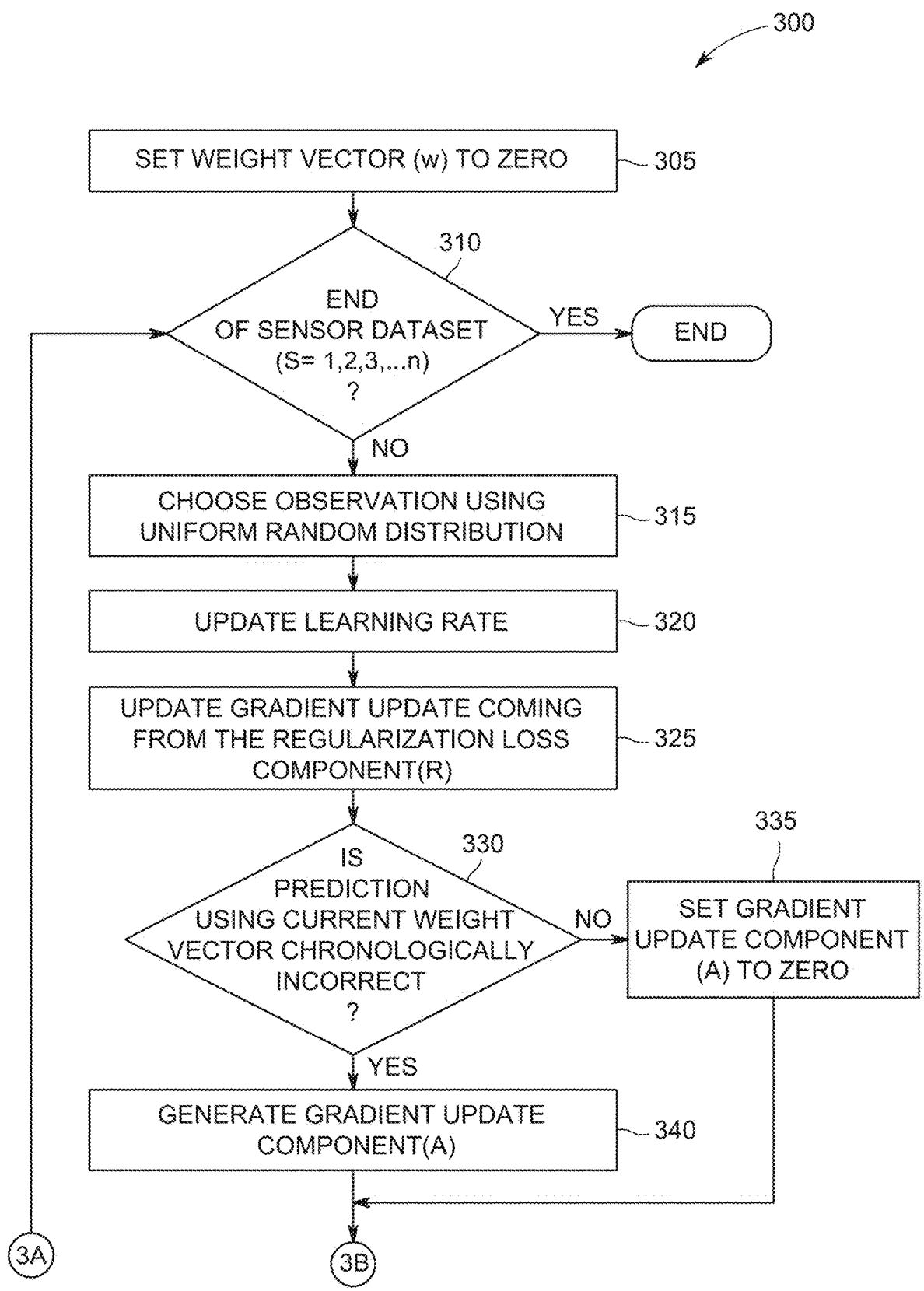
FIGS. 3A-3B depict a flowchart for a process of temporal transductive stochastic gradient descent in accordance with embodiments for a linear model
Figure 3B:
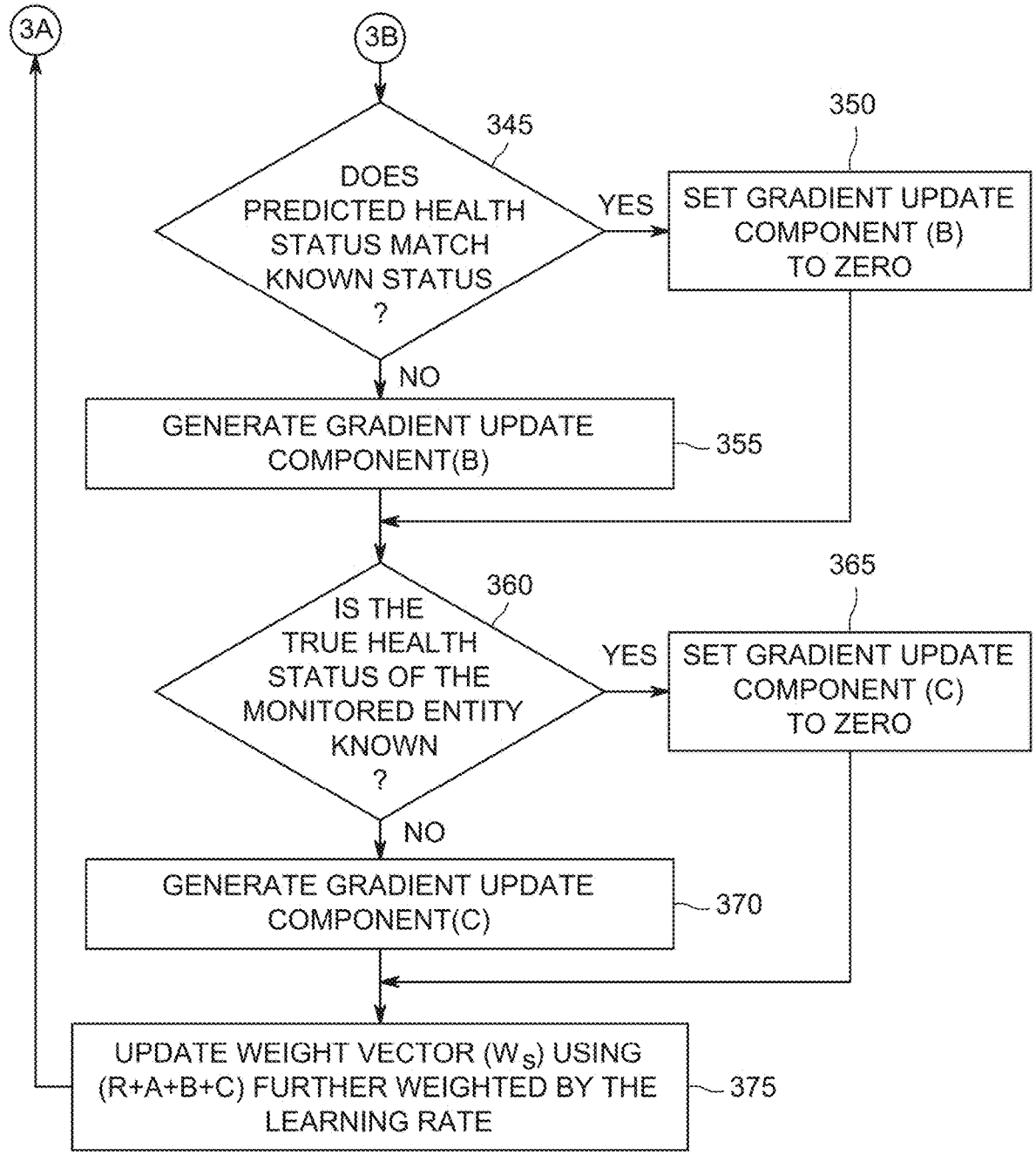

$\quad\quad \delta \leftarrow \delta + (\phi(x_{i_t}) - \phi(x_{i_t+1}))$
$\quad$ end if
$\quad$ if $(x_{i_t}, y_{i_t}) \in \mathbb{L}$ AND $y_{i_t} \langle w_s, \phi(x_{i_t}) \rangle < 1$ then
$\quad\quad \delta \leftarrow \delta - y_{i_t} \phi(x_{i_t})$
$\quad$ end if
$\quad$ if $(x_{i_t}, y_{i_t}) \in \mathbb{U}$ AND $|\langle w_s, \phi(x_{i_t}) \rangle| < 1$ then
$\quad\quad \delta \leftarrow \delta - \text{sign}(\langle w_s, \phi(x_{i_t}) \rangle) \phi(x_{i_t})$
$\quad$ end if
$\quad w_{s+1} \leftarrow w_s - \eta_s \delta$
end for
return w          ▷ The model parameters
end procedure FIGS. 3A-3B depict a flowchart for temporal transductive stochastic gradient descent (TTSGD) process 300 for a linear model in accordance with embodiments. TTSGD process 300 implements Algorithm I for the linear kernel $\phi(X_{i_t}) = X_{i_t}$. Initially the weight vector (w) is set to zero, step 305. For each member of the sensor dataset, step 310, a loop is entered to determine gradient update components. If there are no further dataset members, process 300 ends.

A sensor observation is chosen, step 315, using a random distribution to select the particular observation. The learning rate ($\eta$) is updated, step 320. The learning rate is the speed at which the model is updated. If the learning rate is too fast, then the optimum can be overshot, resulting in oscillations around the optimum; if too slow, then the optimum can be reached at some longer duration. The learning rate can be updated by $\eta \leftarrow 1/(\lambda(s))$, as shown in Algorithm I.

The gradient update is updated ($\delta \leftarrow \lambda w_s$), step 325, to account for regularization loss (R). A determination is made, step 330, as to whether a prediction using the chosen observation (step 315) is chronologically incorrect. This step compares a chosen observation having an unhealthy status with the next sensor data for that monitored entity. Should a prediction based on the next sensor data indicate a healthy status, an error is flagged—recall that a basis condition is set that assumes monitored entities go from healthy to unhealthy states (not unhealthy to healthy states).

If at step 330 a determination is made that the current weight vector is chronologically incorrect, the gradient component (A) is set to zero, step 335. If chronologically correct, process 300 generates an update to gradient component (A), step 340.

A determination is made, step 345, as to whether the predicted health of the monitored entity matches a known health status of the monitored entity. If the predicted does match the known health status, the gradient component (B) is set to zero, step 350. If the predicted and known health statuses do not match, process 300 generates an update to gradient component (B), step 355.

A determination is made, step 360, as to whether the true health status of the monitored entity is known (either healthy or unhealthy). If the true health status is known, the gradient component (C) is set to zero, step 365. If the true health status is not known, process 300 generates an update to gradient component (C), step 370. At step 375, the weight vector ($w_s$) for the particular member of the dataset is updated using the components (R+A+B+C) further weighted by the learning rate (step 320).

Irrespective of the round in which $\nabla_k(w_k : (x_k, y_k))$ is first used for SGD update, its contribution is weighed by the factor $1/\lambda s$ in the s-th iteration. Also, each time $(x_{i_t}, y_{i_t})$ leads to an update (if a corresponding indicator is true), it contributes $y_{i_t} \phi(x_{i_t})$, $\text{sign}(\langle w_k, \phi(x_{i_t}) \rangle) \phi(x_{i_t})$; or $(\phi(x_{i_t+1}) - \phi(x_{i_t}))$ respectively for the three components of the loss. Thus, after s rounds, if $(x_{i_t}, y_{i_t})$ has resulted in updates $l_{i_t}, u_{i_t}, c_{i_t}$-times (for the three components of loss—labeled ($l_{i_t}$), unlabeled ($u_{i_t}$), and chronological ($c_{i_t}$)), then cumulatively, $w_{s+1}$ can be summarized in terms of the number of times each observation $(x_{i_t}, y_{i_t})$ contributes to the update. This can be expressed as shown in equation 4:

$$w_{s+1} = \frac{1}{\lambda_s} \left( \sum_{(x_{i_t}, y_{i_t}) \in \mathbb{L}} l_{i_t} y_{i_t} \phi(X_{i_t}) + \sum_{(x_{i_t}, y_{i_t}) \in \mathbb{U}} u_{i_t} \phi(x_{i_t}) + \sum_{(x_{i_t})(x_{i_t+1}) \in \mathbb{C}} c_{i_t}(\phi(x_{i_t+1}) - \phi(x_{i_t})) \right) \quad \text{EQ. 4}$$

In accordance with embodiments, by substitution using EQ. 4 the predictive model of EQ 1 can be written as Equation 5:

$$\hat{y}_{j_{t'}} = w_s \phi(x_{j_{t'}}) = \quad \text{EQ. 5}$$
$$\frac{1}{\lambda s} \left( \sum_{(x_{i_t}, y_{i_t}) \in \mathbb{L}} l_{i_t} y_{i_t} K(x_{i_t}, x_{j_{t'}}) + \sum_{(x_{i_t}, y_{i_t}) \in \mathbb{U}} u_{i_t} K(x_{i_t}, x_{j_{t'}}) + \sum_{(x_{i_t})(x_{i_t+1}) \in \mathbb{C}} c_{i_t}(K(x_{i_t+1}, x_{j_{t'}}) - K(x_{i_t}, x_{j_{t'}})) \right)$$

In EQ. 5 the kernel representation $K(a, b) = (\phi(a), \phi(b))$ is used. With the resulting predictive model being inner products on the feature transforms $\phi$, a complex Mercer kernel for non-linear transforms of the input feature space can be used. Such an embodiment is presented in Algorithm II. Note that Algorithm II still optimizes for the primal, but due to the nature of the sub-gradient, kernel products can be used to optimize for the primal. In this implementation, $w_s$ is never explicitly calculated, but rather, $\langle w_s, \phi(x_{i_t}) \rangle$ is estimated as $\hat{y}_{i_t}$ using EQ. 5.

ALGORITHM II

Procedure TTSGDKERNEL($\mathbb{X}, \lambda, J$)
$\quad$ l, u, c $\leftarrow$ 0
$\quad$ for s $\leftarrow$ 1, 2,..., S do          ▷ SGD Iterations
$\quad\quad$ Choose $i_s \in \{1, ..., |A|\}$ uniformly at random
$\quad\quad$ if$\langle ; w_s, \phi(x_{i_t}) \rangle > \langle w_s, \phi(x_{i_t+1}) \rangle$ then
$\quad\quad\quad c_{i_t} \leftarrow c_{i_t} - 1$

ALGORITHM II

```
         end if
         if (x_{i_t}, y_{i_t}) > ∈ 𝕃 AND y_{i_t}⟨w_s, φ(x_{i_t})⟩ < 1 then
             l_{i_t} ← l_{i_t} + 1
         end if
         if (x_{i_t}, y_{i_t}) > ∈ 𝕌 AND |⟨w_s, φ(x_{i_t})⟩| < 1 then
             u_{i_t} ← u_{i_t} + 1
         end if
    end for
    return l,u,c                    ▷ The model parameters
end procedure
```

In accordance with embodiments, the convergence rate of the optimization algorithm is independent of the dataset size, labeled as well as unlabeled, but rather depends on the regularization parameter $\lambda$ and the desired accuracy $\epsilon$.

Figure 4A:
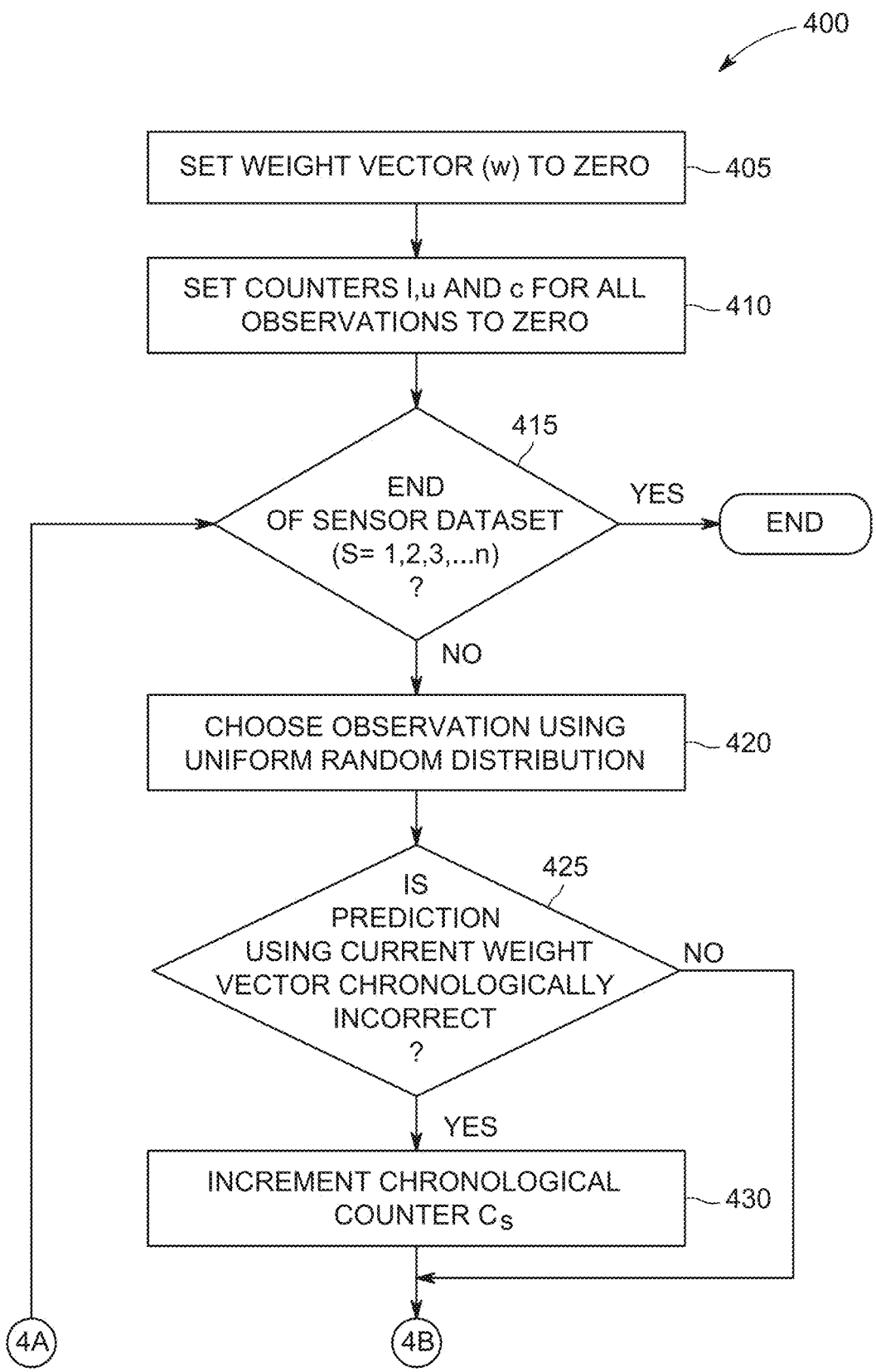
FIGS. 4A-4B depict a flowchart for a process of temporal transductive stochastic gradient descent using a complex kernel to enable non-linear models in accordance with embodiments.
Figure 4B:
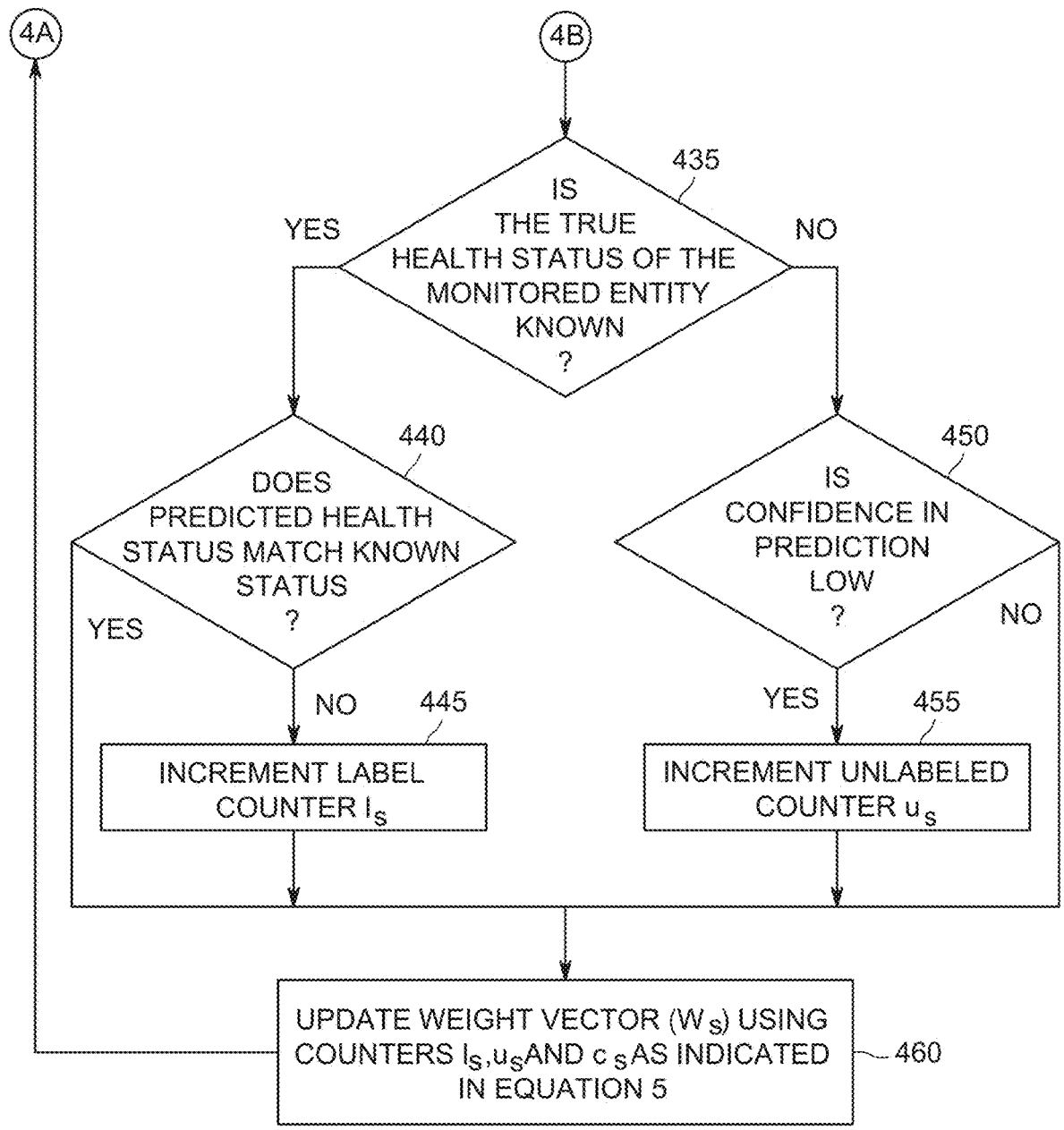

FIGS. 4A-4B depict a flowchart for temporal transductive scholastic gradient descent (TTSGD) process 400 in accordance with embodiments. TTSGD process 400 implements Algorithm II using a complex Mercer kernel to enable non-linear models. Initially the weight vector (w) is set to zero, step 405. Counters representing labeled (l), unlabeled (u), and chronological (c) loss are set to zero, step 410. For each member of the sensor dataset, step 415, a loop is entered to determine gradient update components. If there are no further dataset members, process 400 ends.

A sensor observation is chosen, step 420, using a random distribution to select the particular observation. A determination is made, step 425, as to whether a prediction using the current weight vector is chronologically incorrect. This step compares a chosen observation having an unhealthy status with the next sensor data for that monitored entity. Should a prediction based on the next sensor data indicate a healthy status, an error is flagged—recall that a basis condition is set that assumes monitored entities go from healthy to unhealthy states (not unhealthy to healthy states).

If at step 425 a determination is made that the current weight vector is chronologically incorrect, the chronological counter c is incremented, step 430. If chronologically correct, process 400 continues to step 435.

A determination is made, step 435, as to whether the true health status of the monitored entity is known (either healthy or unhealthy). If the true health status is known, a determination is made as to whether the predicted health of the monitored entity matches a known health status of the monitored entity. If the predicted does match the known health status, process 400 continues to step 460. If the predicted and known health statuses do not match, label counter c is incremented, step 345.

If at step 435 the true health status of the monitored entity is not known, a determination is made regarding the confidence of the predicted health status, step 450. If the confidence in the accuracy of the predicted health status is low, then unlabeled counter u is incremented, step 455. If the confidence in the predicted health status is not low, then process 400 continues to step 460. At step 460, the weight vector ($w_s$) for the particular member of the dataset is updated using counters l, c, and u as described by EQ. 5.

For the TTSGD embodiment of process 300, there is a high probability to find an E-accurate solution in $O(1/\lambda\epsilon)$ iterations. Just like the conventional PEGASOS algorithm, the number of iterations is independent of the number of examples (labeled or unlabeled), but rather depends on the regularization and desired accuracy. For the TTSGD-Kernel approach embodiment of process 400, the runtime can depend on the number of observations, due to the min(s, $|𝕃|+|𝕌|+|ℂ|$) kernel evaluations at iteration s, bringing the overall runtime to $O((|𝕃|+|𝕌|+|ℂ|)/\lambda\epsilon)$. The bounds derived above are for the average hypothesis, but in practice the performance of the final hypothesis can be better.

Algorithm III is pseudocode for a data generation process. The terms N, T, p, a are pre-defined constants; where: N is the total instances to generate, T is a typical length of a series, p is a fraction of instances that will change state, and a is a fraction of the time-series that denotes change. $ℂ_{-/+}$ represents an input binary classification dataset.

ALGORITHM III

```
Procedure DATAGEN(ℂ__,ℂ+)
    𝕏 ← { }
    𝕐 ← { }
    for i ← 1 to N do
        T_i ~ Poisson(T)                      ▷ Length of time-series
        y_iT_i ~ Bernoulli(p)                 ▷ Does y_i changes state?
        If y_iT_i ≠ 0 then
            t_+ ~ Poisson( aT_i)              ▷ Time of change
            y_iT_i ← -1, if 0 ≤ t < t_+
            y_iT_i ← +1, if t_+ ≤ t ≤ T_i
            Draw x_{i,t} uniformly randomly from ℂ_{y_{i,t} y_{i,t}}, with replacement
        else
            y_iT_i ← -1, if 0 ≤ t ≤ T_i
            Draw X_{i,t} uniformly randomly from ℂ__, with replacement
        end if
        𝕏 ← 𝕏 ∪ {x_i}
        𝕐 ← 𝕐 ∪ {y_i}
    end for
    return 𝕏, 𝕐                              ▷ The generated dataset
end procedure
```

Intuitively, the time series of each entity can start from observations from one class (healthy), and then for a select group of entities change over to the other class (unhealthy). Generating datasets in this manner enables the accurate identification of changepoints, since ground truth about change is available for evaluation. Algorithm III describes the process of generating the state-change dataset given any binary classification problem.

Algorithm III is governed by four parameters: (1) number of entities to generate (N); (2) length of time series for entity i (modeled as a random variable drawn from a Poisson distribution with expected value T); (3) fraction of instances that undergo change (modeling the likelihood that a certain entity can undergo change as a Bernoulli distribution with success probability p); and (4) time of change (modeled as a Poisson distribution with expected value $aT_i$ for entity i). Where the factor 'a' can be thought of as roughly the fraction of the time series of entity i that has changed state.

Custom datasets for controlled experiments were created using popular benchmark classification datasets which deal with the identification of onset of certain major disorders, and Algorithm III. The popular benchmark datasets included (a) Pima-Indian Diabetes Smith et al. (1988) (glucose, plasma, serum and skin measurements from individuals of the Pima tribe to identify those which show signs of diabetes); (b) Parkinson Speech dataset Little et al. (2007) (voice measurements from thirty-one people including twenty-three with Parkinson's disease, with roughly 6 measurements from each individual, to identify the diseased); (c) Ovarian Cancer III et al. (2002) (proteomic patterns in serum that distinguish ovarian cancer from non-cancer).

In addition to these datasets from the life-sciences community, also utilized were datasets that have been utilized for comparing SVM classifiers—namely the Adult, MNIST and USPS datasets used in the comparison of scalable SVM algorithms. These are not life-sciences datasets, but are generally applicable as data that changes from one class to another over time, as enabled by Algorithm III.

Table I describes the characteristics of the datasets. In the experiments, T=10, a=0.5, p=0.5 and N was chosen to generate a wide variety of data. Note that the amount of data being classified by the classifier is approximately of the order of NT.

TABLE I

| Dataset | # observations | #features | N |
|---|---|---|---|
| Diabetes | 768 | 8 | 75 |
| Parkinson | 195 | 22 | 20 |
| Ovarian Cancer | 1200 | 5 | 10 |
| Adult | 4884 | 123 | 100 |
| MNIST | 70000 | 780 | 100 |
| USPS | 9298 | 256 | 100 |

Figure 5:
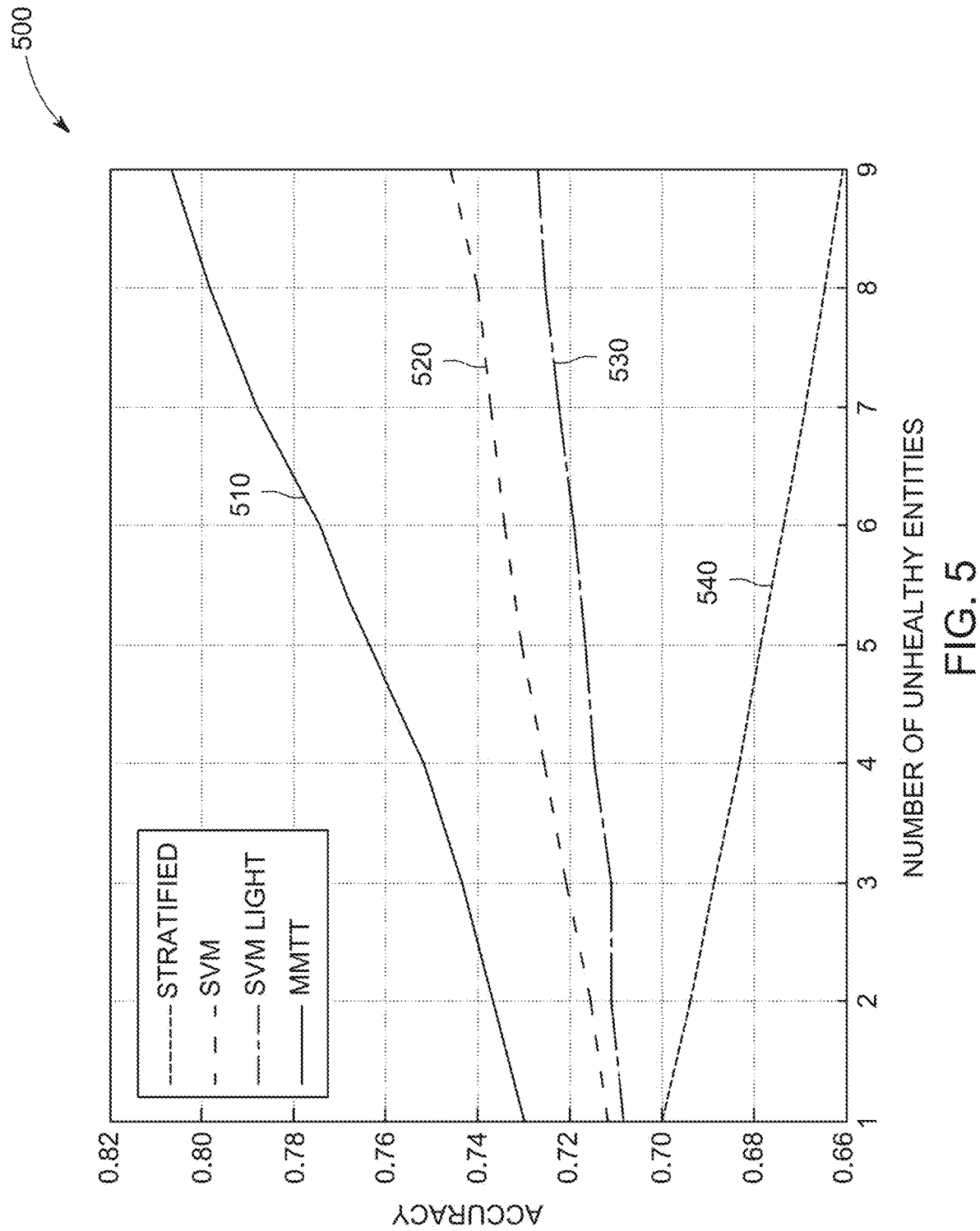
FIG. 5 depicts a comparison of the accuracy of various conventional approaches with an embodying MMTT approach in accordance with embodiments.

FIG. 5 depicts comparison 500 illustrating the accuracy of various conventional approaches with an embodying MMTT approach in accordance with embodiments, where the number of known unhealthy entities is increased. The approaches for this comparison are stratified 540, SVMlight 530, SVM 520, and MMTT 510. The particular dataset of FIG. 5 is for diabetes, however the results shown are representative of the performance for the other data sets (Parkinson, Ovarian Cancer, Adult, MNIST, and USPS).

The accuracy is expressed as a percentage (normalized to 1.0) and is plotted against an increasing number of known unhealthy entities. Increasing the number of known unhealthy entities is akin to the task of attempting to classify all monitored entities given a disease outbreak wherein, the information about few unhealthy entities becomes available at a time. The accuracy is reported on being able to classify all entities at the final diagnoses, as well as all the intermediate predictions leading to the final state. It can be observed that MMTT 510 outperforms all the other approaches, with minimal supervision.

Barring the USPS dataset (not shown), the initial accuracy of MMTT is significantly superior. The particularly weak performance of svmlight (the conventional transductive baseline), might be attributable to the need to maintain a balance of class proportions in the labeled and unlabeled sets. This assumption may not hold in other real-world problem settings. The negative impact of this assumption is more pronounced in the straw-man baseline, the stratified classifier, which by definition, randomly assigns label by class proportions in the labeled set. Its performance worsens as more unhealthy instances are added to the labeled set, thereby skewing the class proportions.

Figure 6:
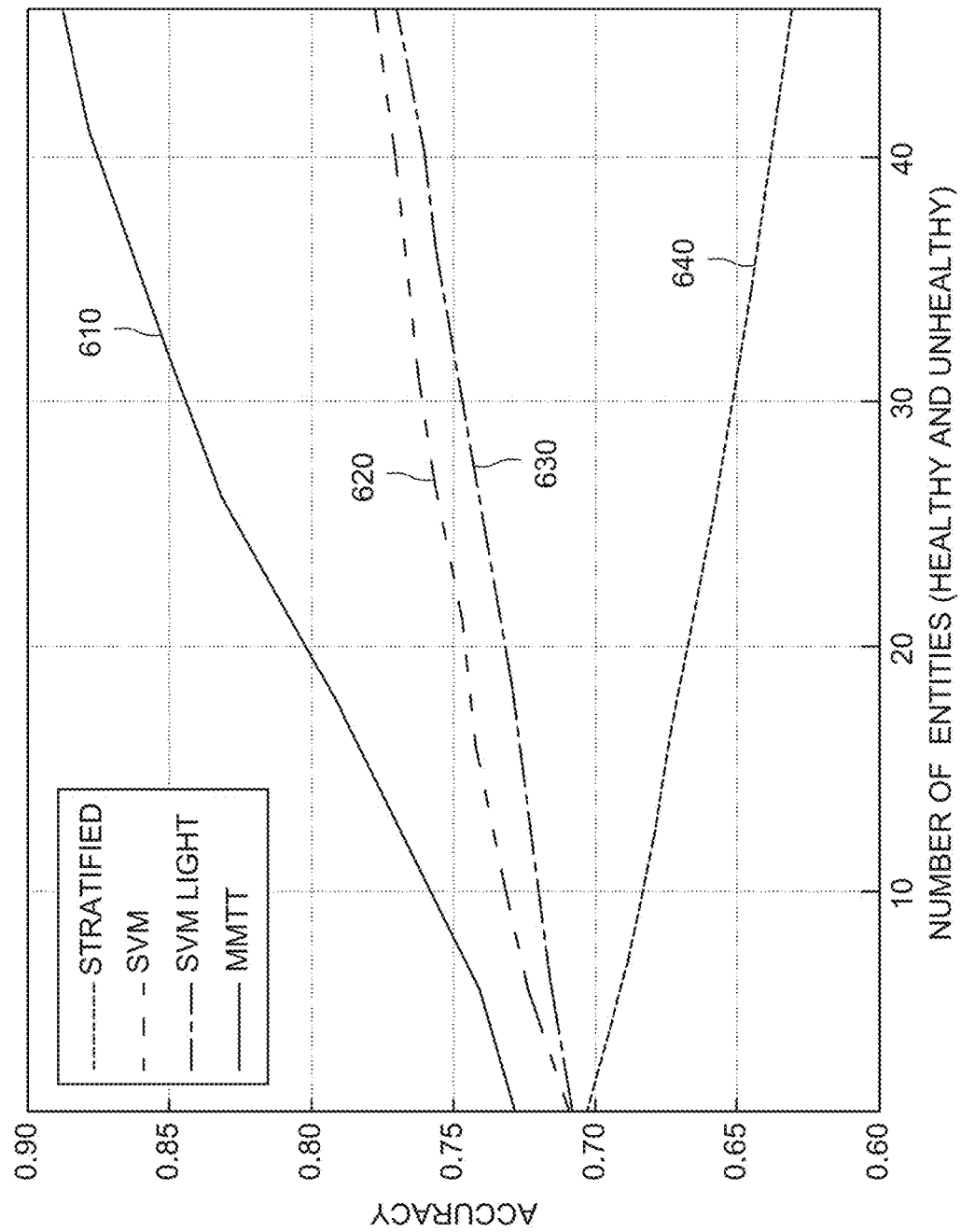
FIG. 6 depicts another comparison of the accuracy of various conventional approaches with an embodying MMTT approach in accordance with embodiments.

Root-cause analysis is another use case where final diagnoses of many/all entities are available and the goal is to classify observations along the time-series for time-of-change identification, enabling investigation of external stimuli concurrent with time of change. FIG. 6 depicts comparison 600 illustrating the accuracy of various conventional approaches with an embodying MMTT approach in accordance with embodiments. The approaches for this comparison are stratified 640, SVMlight 630, SVM 620, and MMTT 610. FIG. 6 presents the trends of accuracy on the various datasets when there is knowledge of final diagnoses of entities—e.g., either a final diagnosis of healthy or unhealthy.

The trends look similar to those in FIG. 5, albeit, the overall performance for all approaches has improved. Even with the knowledge of all final diagnoses, the performance of conventional transduction is sub-par compared to even the induction based simple SVM. It is possible that the implicit strategy of attempting to maintain class proportions across labeled and unlabeled sets leads to poorer performance.

Limited supervision makes parameter tuning particularly challenging. The conventional approach of using cross-validation is unlikely to be applicable. One of the important use-cases for this kind of approach is the detection of problems that have recently cropped up, such as a disease, equipment malfunction or otherwise. If there are only few (e.g., perhaps one, two or three) cases of known problems, mechanisms for arriving at the right parameters through methods that rely on estimating the generalization error through a cross-validation or similar setup are infeasible.

Based on the chronological problem setting, embodying systems and methods offer a remedy for parameter tuning. This being a transductive problem setting, interest resides in the performance on unlabeled sets, not the generalization error. It is well known that estimating this error using the labeled subset is a untenable and might lead to overfitting the labeled set. In this particular problem setting, embodying systems and methods utilize the fact that healthiness only transitions from healthy to unhealthy. In accordance with embodiments, a chronological error $\ell_{chrono}$ is defined. This chronological error is estimated only on the unlabeled subset, as the fraction of violated chronological constraints. This estimate can be used in conjunction with the accuracy on the labeled set $\ell_{labeled}$ to arrive at an estimate of eventual performance on the unlabeled set.

$$\bar{\ell}_{unlabeled} = \frac{|C|}{|C|+|L|} \ell_{chrono} + \frac{|L|}{|C|+|L|} \ell_{labeled} \qquad \text{EQ 6}$$

Figure 7:
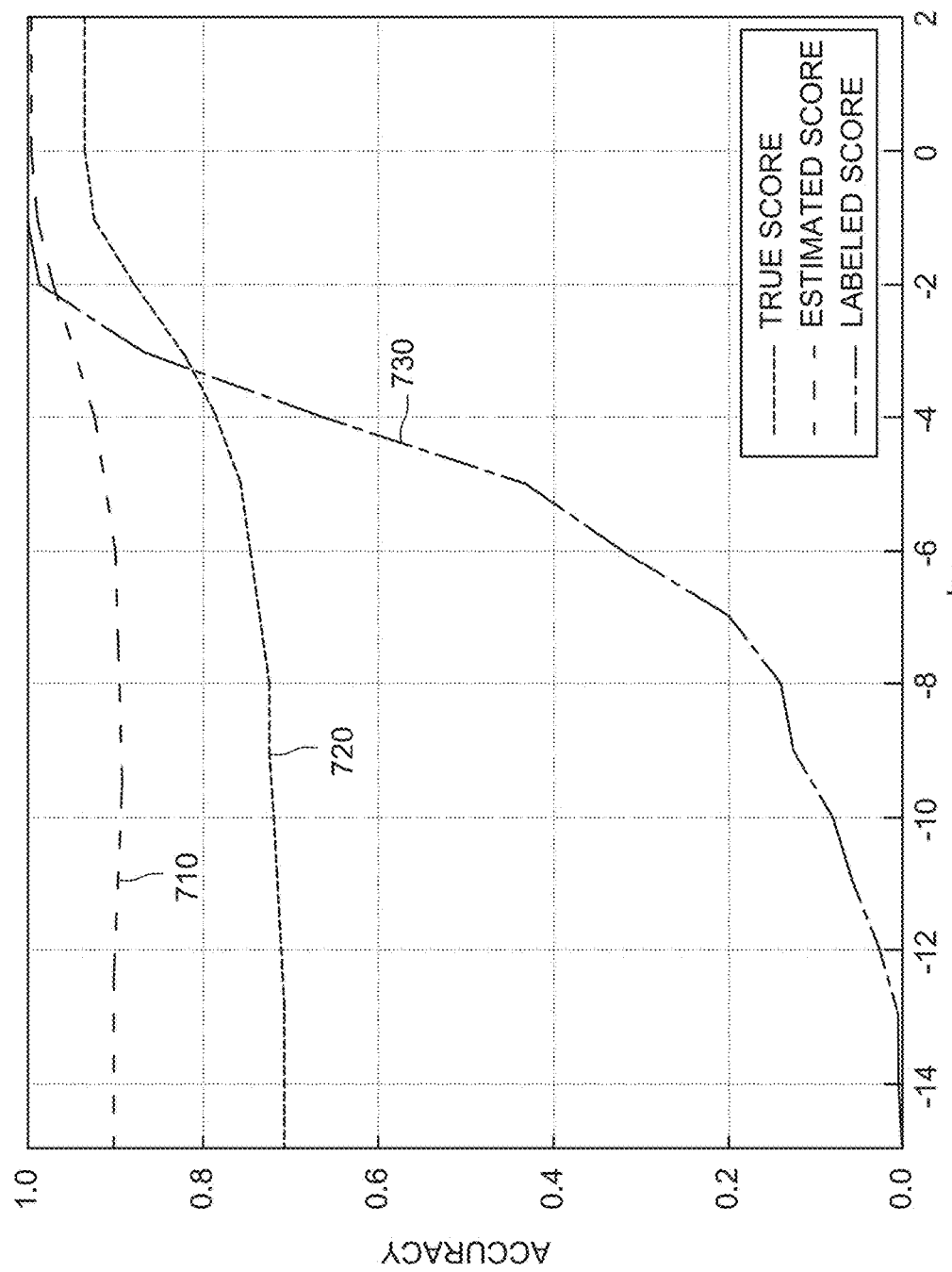
FIG. 7 depicts a comparison of strategies to estimate performance on an unlabeled set for tuning the model parameter in accordance with embodiments.

FIG. 7 depicts comparison 700 of strategies to estimate performance on an unlabeled set for tuning the model parameter in accordance with embodiments. The x-axis represents the parameter being tuned for better performance. The y-axis represents the fraction of correctly classified observations as an accuracy normalized to unity. As shown in comparison 700, for any value of a parameter the estimated score obtained by embodying systems and methods better aligns with the true score, as compared to the score that is derived from the labeled dataset only.

The comparison of FIG. 7 relies on estimates of unlabeled loss from EQ. 6, with true loss 720 and estimated loss 710 based on the labeled set. The estimated unlabeled score tracks the true score better than labeled set score 730, which is likely to overfit the labeled set. It is crucial that the comparison uses the estimate of EQ. 6, rather than just the chrono loss, because a perfect chrono score can be achieved just by labeling all instances as belonging to any one class. The linear combination with labeled score penalizes such scenarios and achieves a more balanced score. The score on the labeled set alone is not good for choosing the right y though and might lead to sub-optimal performance. Thus, EQ. 6 seems to be a valid potential surrogate performance metric for tuning parameters that are likely to achieve better performance on the unlabeled set.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method for max-margin temporal transduction SVM, as disclosed above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

I claim:

1. A method of detecting status changes, and a corresponding point-in-time, in one or more monitored entities, the method comprising:
   receiving, via one or more sensors, one or more signals being representative of an operational state of the one or more monitored entities;
   transferring, via the one or more sensors, one or more elements of time-series data derived from the one or more signals, to a processor being communicatively coupled to the one or more sensors, the time-series data comprising both labeled and unlabeled data;
   wherein the labeled data includes: the initial measurements from all of the monitored entities and the final measurements from monitored entities with known unhealthy states;
   creating a predictive model from the time-series data in a datastore memory;
   applying a transduction classifier to the predictive model, the transduction classifier detecting a change from healthy to unhealthy in the time-series data, and the corresponding point-in-time when the change occurred;
   classifying, by the transduction classifier, the unlabeled data, generating classified data to (i) classify a plurality of final states of monitored entities with unknown final diagnoses to identify those with disorders, and (ii) classify intermediate observations to identify the corresponding point-in-time when the change occurred;
   providing an identification of the change in the time-series data and the corresponding point-in-time; and
   training the predictive model for optimized performance based on the unlabeled data, the labeled data, and the classified data.

2. The method of claim 1, wherein the transduction classifier is a maximum margin classifier having a support vector machine component and a temporal transductive component.

3. The method of claim 2, wherein the maximum margin classifier incorporates a constraint that penalizes a violation in a chronology of events, such that the one or more monitored entities cannot go from unhealthy to healthy without an intervention.

4. The method of claim 2, wherein the maximum margin classifier implements a stochastic gradient descent.

5. The method of claim 2, wherein the maximum margin classifier detects the change in the time-series data by analyzing one element of the time-series data and its next subsequent element.

6. The method of claim 2, wherein applying the maximum margin classifier to the predictive model further includes:
   setting a weight vector to a value of zero;
   for each element of the one or more elements of the time-series data:
   selecting an element of the one or more elements of the time-series data;
   updating a learning rate;
   updating a gradient to account for a regularization loss;
      if the weight vector is chronologically incorrect, setting a first gradient component to zero;
      if the weight vector is chronologically correct, generating an update value for the first gradient component;
      if a health status indicated by a corresponding predictive model member matches a known health status of the selected element, setting a second gradient component to a value of zero;
      if the health status indicated by the corresponding predictive model member does not match the known health status of the selected element, generating an update value for the second gradient component;
      if a true condition of the health status of the selected element is known, setting a third gradient component to a value of zero;
      if a true health status of the selected element is not known, generating an update value for the third gradient component; and
   updating a weight vector for the selected element based on values of the first gradient component, the second gradient component, the third gradient component and the regularization loss component.

7. A non-transitory computer readable medium containing computer-readable instructions stored therein for causing a control processor to perform a method of detecting status changes, and a corresponding point-in-time, in one or more monitored entities, the method comprising:
   receiving, via one or more sensors, one or more signals being representative of an operational state of the one or more monitored entities;

transferring, via the one or more sensors, one or more elements of time-series data derived from the one or more signals, to the processor being communicatively coupled to the one or more sensors, the time-series data comprising both labeled and unlabeled data;

wherein the labeled data includes: initial measurements from all of the monitored entities and final measurements from monitored entities with known unhealthy states;

creating a predictive model from the time-series data in a datastore memory;

applying a transduction classifier to the predictive model;

the transduction classifier detecting a change from healthy to unhealthy in the time-series data, and the corresponding point-in-time when the change occurred;

classifying, by the transduction classifier, the unlabeled data, generating classified data to (i) classify a plurality of final states of monitored entities with unknown final diagnoses to identify those with disorders, and (ii) classify intermediate observations to identify the corresponding point-in-time when the change occurred;

providing an identification of the change in the time-series data and the corresponding point-in-time; and training the predictive model for optimized performance based on the unlabeled data, the labeled data, and the classified data.

8. The non-transitory computer readable medium of claim 7, further comprising computer-readable instructions stored therein to cause the control processor to apply the transduction classifier as a maximum margin classifier having a support vector machine component and a temporal transductive component.

9. The non-transitory computer readable medium of claim 8, further comprising computer-readable instructions stored therein to instruct the control processor to perform the method, including incorporating a constraint, via the maximum margin classifier, that penalizes a violation in a chronology of events, such that the one or more monitored entities cannot go from an unhealthy state to a healthy state without an intervention.

10. The non-transitory computer readable medium of claim 8, further comprising computer-readable instructions stored therein to cause the control processor to perform the method, including implementing a stochastic gradient descent via the maximum margin classifier.

11. The non-transitory computer readable medium of claim 8, further comprising computer-readable instructions stored therein to cause the control processor to perform the method, including detecting the change in the time-series data by analyzing one element of the time-series data and its next subsequent element via the maximum margin classifier.

12. The non-transitory computer readable medium of claim 7, further comprising computer-readable instructions stored therein to cause the control processor to perform the method, including:

setting a weight vector to a value of zero;

for each element of the one or more elements of the time-series data:

selecting an element of the one or more elements of the time-series data;

updating a learning rate;

updating a gradient to account for a regularization loss;

if the weight vector is chronologically incorrect, setting a first gradient component to a value of zero;

if the weight vector is chronologically correct, generating an update value for the first gradient component;

if a health status indicated by a corresponding predictive model member matches a known health status of the selected element, setting a second gradient component to a value of zero;

if the health status indicated by the corresponding predictive model member does not match the known health status of the selected element, generating an update value for the second gradient component;

if a true condition of the health status of the selected element is known, setting a third gradient component to a value of zero;

if a true health status of the selected element is not known, generating an update value for the third gradient component; and updating a weight vector for the selected element based on values of the first gradient component, the second gradient component, the third gradient component and the regularization loss component.

13. A method of detecting status changes, and a corresponding point-in-time, in one or more monitored entities, the method comprising:

receiving, via one or more sensors, one or more signals being representative of an operational state of the one or more monitored entities;

transferring, via the one or more sensors, one or more elements of time-series data derived from the one or more signals, to a processor being communicatively coupled to the one or more sensors the time-series data comprising both labeled and unlabeled data;

wherein the labeled data includes: initial measurements from all of the monitored entities and final measurements from monitored entities with known unhealthy states;

creating a predictive model from the time-series data in a datastore memory;

applying a transduction classifier to the predictive model;

the transduction classifier detecting a change from healthy to unhealthy in the time-series data, and the corresponding point-in-time when the change occurred;

classifying, by the transduction classifier, the unlabeled data, generating classified data to (i) classify a plurality of final states of monitored entities with unknown final diagnoses to identify those with disorders, and (ii) classify intermediate observations to identify the corresponding point-in-time when the change occurred;

incrementing a chronological counter when a prediction based on a current weight vector for a selected element is chronologically incorrect;

incrementing a label counter when (i) a true health status of the selected element is known and (ii) a predicted health status does not match the true health status;

incrementing an unlabel counter when (i) the true health status of the selected element is unknown and (ii) a confidence in the predicted health status is low;

updating the weight vector using the chronological counter, the label counter, and the unlabel counter; and training the predictive model for optimized performance based on the unlabeled data, the labeled data, and the classified data.

14. A system for detecting status changes, and a corresponding point-in-time, in one or more monitored entities, the system comprising:

a server having a control processor and a transductive learning unit, the transductive learning unit including a max-margin temporal classifier unit;

the server in communication with at least one computing device across an electronic network, the at least one computing device having a memory with time-series data; the server configured to receive the time-series data;

the control processor configured to execute executable instructions that cause the system to perform a method of:

receiving, via one or more sensors, one or more signals being representative of an operational state of the one or more monitored entities;

transferring, via the one or more sensors, one or more elements of time-series data derived from the one or more signals, to a processor being communicatively coupled to the one or more sensors, the time-series data comprising both labeled and unlabeled data;

wherein the labeled data includes: initial measurements from all of the monitored entities and final measurements from monitored entities with known unhealthy states;

creating a predictive model from the time-series data in a datastore memory; applying a transductive classifier to the predictive model, the transductive classifier detecting a change from healthy to unhealthy in the time-series data, and the corresponding point-in-time when the change occurred;

classifying, by the transduction classifier, the unlabeled data, generating classified data to (i) classify a plurality of final states of monitored entities with unknown final diagnoses to identify those with disorders, and (ii) classify intermediate observations to identify the corresponding point-in-time when the change occurred;

providing an identification of the change in the time-series data and the corresponding point-in-time; and training the predictive model for optimized performance based on the unlabeled data, the labeled data, and the classified data.

15. The system of claim 14, wherein the executable instructions include instructions to cause the control processor to apply the transduction classifier as a maximum margin classifier having a support vector machine component and a temporal transductive component.

16. The system of claim 15, wherein the executable instructions include instructions to cause the control processor to perform the method including incorporating a constraint, via the maximum margin classifier, that penalizes a violation in a chronology of events, such that the one or more monitored entities cannot go from an unhealthy state to a healthy state without an intervention.

17. The system of claim 15, wherein the executable instructions include instructions to cause the control processor to perform the method including the maximum margin classifier implementing a stochastic gradient descent.

18. The system of claim 16, wherein the executable instructions include instructions to cause the control processor to perform the method including the maximum margin classifier detecting the change in the time-series data by analyzing one element of the time-series data and its next subsequent element.

19. The system of claim 14, wherein the executable instructions include instructions to cause the control processor to perform the method including:

setting a weight vector a value of zero;

for each element of the one or more elements of the time-series data:

selecting of the time-series data;

updating a learning rate;

updating a gradient to account for a regularization loss;

if the weight vector is chronologically incorrect, setting a first gradient component to zero;

if the weight vector is chronologically correct, generating an update value for the first gradient component;

if a health status indicated by a corresponding predictive model member matches a known health status of the selected element, setting a second gradient component to a value of zero;

if the health status indicated by the corresponding predictive model member does not match the known health status of the selected element, generating an update value for the second gradient component;

if a true condition of the health status of the selected element is known, setting a third gradient component to a value of zero;

if a true health status of the selected element is not known, generating an update value for the third gradient component; and updating a weight vector for the selected element based on values of the first gradient component, the second gradient component, the third gradient component and the regularization loss component.

20. The system of claim 15, wherein the executable instructions include flagging an error if a prediction based on a subsequent element of the time-series data indicating a healthy state after a preceding element indicated an unhealthy state.

* * * * *